US011419350B2

(12) United States Patent
Rakitsky et al.

(10) Patent No.: US 11,419,350 B2
(45) Date of Patent: Aug. 23, 2022

(54) FEED INGREDIENTS COMPRISING LYSED MICROBIAL CELLS

(71) Applicant: Corbion Biotech, Inc., South San Francisco, CA (US)

(72) Inventors: Walter Rakitsky, San Diego, CA (US); John Piechocki, South San Francisco, CA (US); Wenhua Lu, South San Francisco, CA (US); Janice Wee, San Mateo, CA (US); Jorge Galazzo, Sunnyvale, CA (US)

(73) Assignee: CORBION BIOTECH, INC., South San Francisco, CA (US)

( * ) Notice: Subject to any disclaimer, the term of this patent is extended or adjusted under 35 U.S.C. 154(b) by 0 days.

(21) Appl. No.: 15/636,506

(22) Filed: Jun. 28, 2017

(65) Prior Publication Data

US 2018/0000130 A1 Jan. 4, 2018

Related U.S. Application Data

(60) Provisional application No. 62/408,630, filed on Oct. 14, 2016, provisional application No. 62/357,829, filed on Jul. 1, 2016.

(51) Int. Cl.
*A23K 50/80* (2016.01)
*A23K 10/00* (2016.01)
(Continued)

(52) U.S. Cl.
CPC .............. *A23K 50/80* (2016.05); *A23K 10/00* (2016.05); *A23K 10/16* (2016.05); *A23K 10/18* (2016.05);
(Continued)

(58) Field of Classification Search
CPC ........ A23K 50/80; A23K 10/00; A23K 10/16; A23K 10/18; A23K 10/20; A23K 10/22;
(Continued)

(56) References Cited

U.S. PATENT DOCUMENTS 4,333,611 A 6/1982 Zucker et al.
5,518,918 A * 5/1996 Barclay .................. A61K 31/20
435/257.1
(Continued)

FOREIGN PATENT DOCUMENTS

CN 103131529 B 2/2016
CN 106833876 A 6/2017
(Continued)

OTHER PUBLICATIONS

Acharya, Deependra, "Fillet Quality and Yield of Farmed Atlantic Salmon (*Salmo salar* L.): variation between families, gender differences and the importance of maturation", Norwegian University of Life Sciences, Department of Animal and Aquacultural Science, 2011 Masters Thesis, (Apr. 27, 2012), http://hdl.handle.net/11250/186065.
(Continued)

*Primary Examiner* — Trevor Love
(74) *Attorney, Agent, or Firm* — Oliff PLC

(57) ABSTRACT

The present disclosure relate to feed ingredients and formulated feed, methods for their manufacture, and uses thereof in nutritional applications such as in aquaculture, terrestrial animal feed, and human nutrition. The feed ingredient compositions comprise lysed microbial cells with a small aspect ratio and triglyceride oil.

16 Claims, 7 Drawing Sheets

(51) Int. Cl.

| | |
|---|---|
| ***A23K 10/16*** | (2016.01) |
| ***A23K 10/18*** | (2016.01) |
| ***A23K 10/20*** | (2016.01) |
| ***A23K 10/22*** | (2016.01) |
| ***A23K 20/00*** | (2016.01) |
| ***A23K 20/158*** | (2016.01) |
| ***A61K 31/202*** | (2006.01) |
| ***A61K 9/16*** | (2006.01) |
| ***A61K 36/02*** | (2006.01) |

(52) U.S. Cl.

CPC .............. *A23K 10/20* (2016.05); *A23K 10/22* (2016.05); *A23K 20/00* (2016.05); *A23K 20/158* (2016.05); *A61K 9/167* (2013.01); *A61K 31/202* (2013.01); *A61K 36/02* (2013.01); *Y02A 40/818* (2018.01)

(58) Field of Classification Search

CPC ...... A23K 20/00; A23K 20/158; A61K 9/167; A61K 31/202; A61K 36/02; Y02A 40/818

See application file for complete search history.

(56) References Cited

U.S. PATENT DOCUMENTS

| | | | |
|---|---|---|---|
| 6,000,551 | A | 12/1999 | Kanel et al. |
| 6,241,472 | B1 | 6/2001 | Bosch et al. |
| 6,355,280 | B1 | 3/2002 | Segal et al. |
| 6,372,460 | B1 * | 4/2002 | Gladue ................. C12P 7/6472 435/134 |
| 6,402,065 | B1 | 6/2002 | Higgins |
| 7,045,143 | B1 | 5/2006 | Sawatzki et al. |
| 8,580,540 | B2 | 11/2013 | Dillon et al. |
| 8,691,293 | B2 | 4/2014 | Gurin |
| 9,115,332 | B2 | 8/2015 | Dillon et al. |
| 9,862,910 | B2 | 1/2018 | Hassan et al. |
| 2001/0041358 | A1 | 11/2001 | Yokochi et al. |
| 2002/0081366 | A1 | 6/2002 | Cain et al. |
| 2003/0138477 | A1 | 7/2003 | Barclay |
| 2003/0143659 | A1 | 7/2003 | Bijl et al. |
| 2003/0157175 | A1 | 8/2003 | Fuchs et al. |
| 2004/0047969 | A1 | 3/2004 | Wester et al. |
| 2004/0109881 | A1 | 6/2004 | Bertholet et al. |
| 2005/0067726 | A1 | 3/2005 | Yan et al. |
| 2005/0100881 | A1 | 5/2005 | Johal |
| 2006/0160203 | A1 | 7/2006 | Barclay |
| 2006/0286205 | A1 | 12/2006 | Fichtali et al. |
| 2007/0003686 | A1 | 1/2007 | Fichtali et al. |
| 2007/0117135 | A1 | 5/2007 | Willimann |
| 2008/0050476 | A1 | 2/2008 | Holdridge et al. |
| 2008/0254119 | A1 | 10/2008 | Dai et al. |
| 2010/0086638 | A1 * | 4/2010 | Kyle ...................... A61K 36/02 426/2 |
| 2010/0167339 | A1 | 7/2010 | Clayton et al. |
| 2010/0239712 | A1 | 9/2010 | Brooks et al. |
| 2010/0297295 | A1 * | 11/2010 | Brooks .................. A21D 2/165 426/61 |
| 2011/0159167 | A1 | 6/2011 | Ruesing et al. |
| 2011/0250680 | A1 | 10/2011 | Broyer et al. |
| 2011/0256282 | A1 | 10/2011 | Piechocki et al. |
| 2012/0091235 | A1 | 4/2012 | Li et al. |
| 2012/0135479 | A1 | 5/2012 | Dillon et al. |
| 2014/0093945 | A1 | 4/2014 | Dillon et al. |
| 2015/0017304 | A1 | 1/2015 | Stefanski et al. |
| 2015/0223483 | A1 | 8/2015 | Syed et al. |
| 2016/0286832 | A1 | 10/2016 | Block et al. |
| 2017/0051230 | A1 | 2/2017 | Hassan et al. |
| 2017/0119005 | A1 | 5/2017 | Piechocki et al. |
| 2017/0218326 | A1 | 8/2017 | Bourdat et al. |
| 2017/0290356 | A1 | 10/2017 | Silva et al. |
| 2017/0306289 | A1 | 10/2017 | Chung et al. |
| 2018/0002711 | A1 | 1/2018 | Schur et al. |
| 2018/0087003 | A1 | 3/2018 | Hassan et al. |
| 2018/0110254 | A1 | 4/2018 | Gierke et al. |
| 2018/0235257 | A1 | 8/2018 | Wozniak |

FOREIGN PATENT DOCUMENTS

| | | | | |
|---|---|---|---|---|
| EP | 0251018 | B1 | 1/1988 | |
| EP | 0522470 | A1 | 1/1993 | |
| EP | 2914124 | B1 | 1/2017 | |
| GB | 2 437 909 | A | 11/2007 | |
| WO | 91/07498 | A1 | 5/1991 | |
| WO | 1991/007498 | A1 | 5/1991 | |
| WO | WO199408467 | | 4/1994 | |
| WO | 1999/065585 | A1 | 12/1999 | |
| WO | 02/00028 | A1 | 1/2000 | |
| WO | 2001/053512 | A1 | 7/2001 | |
| WO | 2002/000028 | A1 | 1/2002 | |
| WO | WO2002010423 | | 2/2002 | |
| WO | 2002/072742 | A1 | 9/2002 | |
| WO | WO2003013271 | A1 | 2/2003 | |
| WO | WO2004036982 | A2 | 5/2004 | |
| WO | WO2004082399 | | 9/2004 | |
| WO | 2005/027651 | A1 | 3/2005 | |
| WO | 2006/124598 | A2 | 11/2006 | |
| WO | WO2006122299 | | 11/2006 | |
| WO | 2007/117511 | A2 | 10/2007 | |
| WO | 2007/121273 | A2 | 10/2007 | |
| WO | 2010/006765 | A1 | 1/2010 | |
| WO | 2010/018049 | A1 | 2/2010 | |
| WO | 2010/045368 | A2 | 4/2010 | |
| WO | WO2010107415 | | 9/2010 | |
| WO | 2010/120939 | A2 | 10/2010 | |
| WO | WO2010120923 | A1 | 10/2010 | |
| WO | 2010/138620 | A1 | 12/2010 | |
| WO | WO2011031166 | | 3/2011 | |
| WO | WO2011054800 | | 5/2011 | |
| WO | 2011/130576 | A1 | 10/2011 | |
| WO | 2011/130578 | A2 | 10/2011 | |
| WO | 2013/010090 | A2 | 1/2013 | |
| WO | WO2013040732 | A1 | 3/2013 | |
| WO | 2014/043053 | A1 | 3/2014 | |
| WO | 2014/122087 | A1 | 8/2014 | |
| WO | 2014/122092 | A1 | 8/2014 | |
| WO | 2015/073770 | A1 | 5/2015 | |
| WO | 2015/095690 | A2 | 6/2015 | |
| WO | WO2015095694 | | 6/2015 | |
| WO | WO2015099817 | | 7/2015 | |
| WO | 2016/050559 | A1 | 4/2016 | |
| WO | WO-2016050559 | A1 * | 4/2016 | ........... A23K 20/158 |
| WO | WO2016154490 | | 9/2016 | |
| WO | WO2017093449 | A1 | 6/2017 | |
| WO | WO2017198176 | | 11/2017 | |
| WO | 2018/002374 | A1 | 1/2018 | |
| WO | 2018/002377 | A1 | 1/2018 | |
| WO | WO2018011286 | A1 | 1/2018 | |
| WO | WO2018156596 | | 8/2018 | |

OTHER PUBLICATIONS

Ackman, Robert G., "The gas chromatograph in practical analyses of common and uncommon fatty acids for the 21st century", *Analytica Chimica Acta*, (Aug. 16, 2002), vol. 465, Issues 1-2, pp. 175-192.

Bligh, E.G. and W.J. Dyer, "A Rapid Method of Total Lipid Extraction and Purification", *Canadian Journal of Biochemistry and Physiology*, (Aug. 1959), issued by the National Research Council of Canada, vol. 37, No. 8, pp. 911-917.

Dumas, Andre et al., "Quantitative description of body composition and rates of nutrient deposition in rainbow trout (*Oncorhynchus mykiss*)", *Aquaculture*, (Nov. 30, 2007), vol. 273, Issue 1, pp. 165-181.

Kousoulaki, Katerina, et al., "Metabolism, health and fillet nutritional quality in Atlantic salmon (*Salmo salar*) fed diets containing n-3-rich microalgae", *Journal of Nutritional Science*, (Jun. 11, 2015), vol. 4 (e24). http://doi.org/10.1017/jns.2015.14.

Kousoulaki K., et al., "Microalgae and organic minerals enhance lipid retention efficiency and fillet quality in Atlantic salmon (*Salmo salar* L.)", *Aquaculture*, (Jan. 20, 2016), vol. 451, pp. 47-57.

(56) References Cited

OTHER PUBLICATIONS

McNivena, M.A. et al., Ratio of n-6/n-3 in the diets of beef cattle: Effect on growth, fatty acid composition, and taste of beef, *Animal Feed Science and Technology*, (Dec. 22, 2011), vol. 170, Issues 3-4, pp. 171-181.

Rosenlund, Grethe et al., "Atlantic salmon require long-chain n-3 fatty acids for optimal growth throughout the seawater period," *Journal of Nutritional Science*, (May 11, 2016), vol. 5 (e19), 13 pages, http://doi:10.1017/jns.2016.10.

Sprague, M. et al., "Impact of sustainable feeds on omega-3 long-chain fatty acid levels in farmed Atlantic salmon, 2006-2015", *Science Reports*, (Feb. 22, 2016), vol. 6, Article No. 21892, http://doi:10.1038/srep21892.

Sukhija, Pritam S. and D. L. Palmquist, "Rapid Method for Determination of Total Fatty Acid Content and Composition of Feedstuffs and Feces", *Journal of Agricultural and Food Chemistry*, (Nov. 1988), vol. 36, No. 6, pp. 1202-1206.

Waagbo, Rune et al., "Chemical and sensory evaluation of fillets from Atlantic salmon (*Salmo salar*) fed three levels of N-3 polyunsaturated fatty acids at two levels of vitamin E", *Food Chemistry*, (Jan. 1, 1993) vol. 46, Issue 4, pp. 361-366, https://doi.org/10.1016/0308-8146(93)90005-Z.

Wolters, William R., et al., "Growth parameters of wild and selected strains of Atlantic salmon, *Salmo salar*, on two experimental diets", *Aquaculture*, (Dec. 1, 2009), vol. 297, pp. 136-140.

Invitation to Pay Additional Fees, dated Oct. 13, 2017, for International Patent Application No. PCT/US2017/040087.

Notification of Transmittal of the International Search Report and the Written Opinion of the International Searching Authority, the International Search Report and the Written Opinion of the Searching Authority, dated Dec. 12, 2017, for International Patent Application No. PCT/US2017/040087, 21 pages.

International Preliminary Report on Patentability Chapter I, dated Jan. 1, 2019, for International Patent Application No. PCT/US2017/040087, 21 pages.

Oct. 27, 2021 Office Action issued in Chinese Patent Application No. 201780036267.8.

Translation of "Biochemistry", edited by Yongmin Wang et al., China Light Industry Press, first edition, Feb. 2017, p. 36.

Translation of "Animal Nutrition and Feeds", edited by Li Zhang et al., China Agricultural University Press, first edition. Aug. 2007, pp. 133-134.

Mar. 30, 2022 Office Action issued in Chinese Patent Application No. 201780036267.8.

May 25, 2022 Office Action issued in European Patent Application No. 17740185.8.

* cited by examiner

FEED INGREDIENTS COMPRISING LYSED MICROBIAL CELLS

CROSS-REFERENCE TO RELATED APPLICATIONS

This application claims the benefit under 35 USC 119(e) of U.S. Provisional Patent Application No. 62/357,829, filed Jul. 1, 2016, entitled "FEED INGREDIENTS CONTAINING LYSED MICROBIAL CELLS", and U.S. Provisional Patent Application No. 62/408,630, filed Oct. 14, 2016, entitled "FEED INGREDIENTS CONTAINING OXIDATIVELY STABLE UNLYSED AND LYSED MICROBIAL CELLS", each of which is incorporated herein by reference in its entirety.

BACKGROUND

Triglycerides oils produced by microorganisms and plants provide essential nutrients for consumption by organisms higher in the food chain. Such triglycerides oils are composed of certain fatty acids that are not found or that are produced in lower amounts in the higher order organisms.

BACKGROUND

Triglycerides oils produced by microorganisms and plants provide essential nutrients for consumption by organisms higher in the food chain. Such triglycerides oils are composed of certain fatty acids that are not found or that are produced in lower amounts in the higher order organisms.

Of particular nutritional importance in the food chain are triglycerides oils produced by microorganisms and plants that are high in polyunsaturated fatty acids (PUFA). Polyunsaturated fatty acids include long chain omega-3 fatty acids such as docosahexaenoic acid (DHA). DHA is an important component in human nutrition especially for infants. Aquatic animals such as fish and shellfish also require DHA in their diet for proper development and growth. Additionally, feeding DHA to newly born domesticated animals such as pigs, cows and other mammals increases the survival rate of piglets, calves, kids and other new-born mammals.

A major source of commercial long chain omega-3 fatty acids today is fish oil. About one million metric tons of fish oil are produced each year for use mainly for feed applications in aquaculture, terrestrial animal feed, and human nutrition. The aquaculture industry is growing, but the availability of long chain omega-3 fatty acids from wild caught fish has not increased with demand. Continued availability depends on sustainable fishery management policies, productivity of natural systems that are sensitive to climate changes, and other factors. Many countries have strict quotas on wild caught fish.

SUMMARY

In one embodiment, provided is a feed ingredient composition comprising a dispersion of lysed microbial cells in triglyceride oil, wherein:

a) 5-90% by weight of the composition is lysed cells, and
b) 10-90% by weight of the composition is triglyceride oil, wherein the triglyceride oil comprises oil from the lysed cells and oil from another organism.

In some embodiments, the triglyceride oil has a fatty acid profile of 10-70% docosahexaenoic acid (DHA) by weight, 15%-65% DHA by weight, 20%-60% DHA by weight, 25%-55% DHA by weight, 30%-55% DHA by weight, or 40%-55% DHA by weight, of fatty acids.

In some embodiments, the DHA is 4%-45%, 4%-40%, 4%-35%, 4%-30%, 4%-25% by weight of the composition. In other embodiments, the DHA is 4%-20%, 4%-15%, 5%-15%, 5%-12%, 5%-10%, 5%-7%, 5%-8%, 6%-8%, or 6%-7% by weight of the composition.

In some embodiments, the compositions provided herein comprise 5%-15%, 5%-10%, 10%-15%, 10%-25%, 15%-20%, or 20%-25%, 30%-40%, 30%-50%, 30%-60%, 30%-70%, 30%-80%, 30%-90%, by weight lysed microbial cells.

In some embodiments, the compositions provided herein further comprise less than 20%, 15%, 10%, 5%, 3%, or 1% by weight unlysed microbial cells or wherein the composition is free from unlysed microbial cells. In some embodiments, the compositions are free from unlysed microbial cells In some embodiments, the oil from the lysed microbial cells has a fatty acid profile of 40-70%, 40-50%, 40-50%, 45-55%, or 50-55% DHA by weight of fatty acids.

In some embodiments, the lysed cells have an aspect ratio of less than 1:1. In other embodiments the lysed cells have an aspect ratio of 1:2, 1:3, 1:4, 1:5, 1:6, 1:7, 1:8, 1:9 or 1:10. In some embodiments, the lysed cells have an aspect ratio of 1:2-1.5, 1:2-1:4 or 1:2-1:3. In an embodiment, the lysed cells have an aspect ratio of between 1:1 and 1:5, between 1:5 and 1:10, between 1:10 and 1:15, or between 1:15 and 1:20.

In some embodiments, the lysed cells have a median particle size of from 1-20 micrometers, 1-18 micrometers, 1-15 micrometers, 1-12 micrometers, 1-10 micrometers, 1-9 micrometers, 1-8 micrometers, 1-7 micrometers, 1-6 micrometers, 1-5 micrometers, 1-4 micrometers, 1-3 micrometers, 5-100 micrometers, 5-90 micrometers, 5-80 micrometers, 5-80 micrometers, 5-70 micrometers, 5-60 micrometers, 5-50 micrometers, 5-40 micrometers, 5-30 micrometers, 5-20 micrometers, or 5-10 micrometers.

In some embodiments, greater than half of the lysed cells remain suspended in the composition for at least a week without settling.

In some embodiments, the oil from another organism is oil from a fish, plant, oleaginous microbe or combinations thereof. Such oils include those that are extracted and separated from the another organism. In some embodiments the another microorganism is microalgae, fungus, or yeast.

In some embodiments, the oil from a plant is a coconut, corn, cottonseed, olive, palm, peanut, rapeseed, canola, safflower, sesame, soybean, soybean oil, nut oil, camelina oil, or citrus oil, or one or more combinations thereof.

In some embodiments, the oil from a fish is from an anchovie, herring, menhaden, anchovy, pilchard, sardine, or mackerel or one or more combinations thereof.

In some embodiments, the microbial cells are from the family Thraustochytriaceae.

In some embodiments, the microbial cells are from the genus selected from the group consisting of *Cryptheco-dinium, Thraustochytrium, Aurantiochytrium*, and *Schizochytrium.*

In some embodiments the microbial cells are adapted to grow in low chloride conditions.

In some embodiments, the compositions provided herein further comprise lecithin.

In some embodiments, the compositions provided herein further comprise dietary additions such as micronutrients. Dietary additions include astaxanthin, carotenoids, flavonoids, sterols, chalcitriols (Vitamin D), tocopherols (vitamin E), and phylloquinones and menaquinones (vitamin K).

Other dietary additions include antibiotics, antifungals, antiparasitics, and hormones. Astaxanthins, carotenoids and other dietary additions can be added in the form of microbial biomass. For example, yeast, bacteria, fungi, microalgae or other microorganisms that produce astaxanthins, carotenoids and other micronutrients can be added to the composition.

In some embodiments, the compositions provided herein further comprise an antioxidant. In other embodiments, the antioxidant is a natural antioxidant, lecithin, starch, ascorbic acid, tocopherols, rosemary extract, green tea extract, ascorbyl palmitate butylated hydroxytoluene (BHT), tert-butylhydroquinone (TBHQ), ethoxyquin, or one or more combinations thereof.

In some embodiments, provided is a shipping or storage container comprising the compositions provided herein. In other embodiments, the container is a 55 gallon drum or a tote tank.

In some embodiments, provided is a method for preparing a food ingredient composition provide herein comprising:

a) blending microbial cells and the oil from another organism to form a blend;

b) lysing the microbial cells in the blend to form the composition as a dispersion.

In some embodiments, provided is a method for preparing a formulated feed, comprising contacting the composition provided herein with an edible food.

In some embodiments, provided is a formulated feed comprising a composition provided herein and edible food.

In some embodiments, the edible food is coated with the composition. In other embodiments, the edible food is coated with the composition under vacuum.

In some embodiments, the edible food is an aquaculture or animal feed. In other embodiments, the edible food is a salmon feed. In other embodiments, the edible food comprises fish or animal by-products or combinations thereof.

In some embodiments, the formulated feed is in a pelletized form.

In some embodiments, the formulated feed contains at least 1%, 1.5%, or 2% omega-3 fatty acids.

In some embodiments, the composition provided herein represents at least 10, 15, 20, 25, 30, 35, or 40% by weight of the formulated feed.

In some embodiments, the slurry of the invention is no longer spontaneously combustible. Microbial cells that contain high amounts of PUFA are oxidatively unstable. Storage and transport of microbial cells that contain high amounts of PUFA can be problematic because of its propensity to spontaneously combust. The dispersion of lysed microbial cells in triglyceride oil does not spontaneously combust when subjected to temperatures of between 50° C. and 150° C. In some embodiments, the combustion of the composition or the dispersion of lysed microbial feed ingredient does not occur for at least 5, 6, 7, 8, 9, 10, 11, 12, 13, 14, 15, 16, 17, 18, 19, or 20 hours when the composition or feed formulation is subjected to 80° C. The slurry of the invention is less expensive to ship and insure because it does not spontaneously combust.

The slurry of the invention also minimizes the volume required to ship a given amount of microbial cells. The unlysed microbial cells have low bulk density. The dispersion of the lysed cells and triglyceride oil significantly increases the bulk density of the solids (eliminates air space between agglomerates) such that nearly twice as much biomass fits in the same space. Thus leading to reduced shipping and storage costs. Moreover, the dispersion of the invention is more easily isolated from exposure to oxygen. Purging a super sack of dry biomass with nitrogen is difficult and requires significant amounts of nitrogen and it is difficult to achieve low levels of residual oxygen. In contrast, purging the small headspace in a tote tank containing the slurry of the invention is accomplished easily and with far less nitrogen.

In some embodiments, the composition or the feed ingredient provided herein comprises at least one or more antioxidants selected from the group consisting of lecithin, starch, ascorbic acid, tocopherols, rosemary extract, green tea extract, ascorbyl palmitate, BHT, TBHQ, and PWL. In some embodiements, the two or more antioxidants delay or inhibit the combustion of the biomass when subjected to temperatures of between 50° C. and 150° C. In some embodiments, the combustion of the composition or the feed ingredient does not occur for at least 5, 6, 7, 8, 9, 10, 11, 12, 13, 14, 15, 16, 17, 18, 19, or 20 hours when the composition or feed formulation is subjected to 80° C.

In some embodiements, there is provided a composition comprising microalgal cells of the genus *Crypthecodinium, Thraustochytrium, Aurantiochytrium*, or *Schizochytrium* and two or more antioxidants selected from the group consisting of lecithin, starch, ascorbic acid, tocopherols, rosemary extract, green tea extract, ascorbyl palmitate, BHT, TBHQ, and PWL. The microalgal cells of the composition do not combust for at least 5, 6, 7, 8, 9, 10, 11, 12, 13, 14, 15, 16, 17, 18, 19, or 20 hours when the composition or feed formulation is subjected to 80° C.

In some embodiments, a method of increasing the body weight of an animal is provided. The method comprises feeding the animal with feed that is coated with a dispersion of lysed microbial cells in triglyceride oil wherein the lysed cells have an aspect ratio of less than 1:1.

The dispersion of the lysed microbial cells in triglyceride oil contains from 5% to 90% by weight lysed cells and between 10% to 95% triglyceride oil wherein the triglyceride oil comprises oil from lysed microbial cells and oil from another organism. As an example, a slurry made with 50 g *Schizochytrium* cells containing 50% lipid and 50 grams of canola oil would have a total of 75 g oil (50 g canola oil and 25 g *Schizochytrium* oil.).

In some embodiments, a method of increasing the thermal unit growth coefficient (TGC), the feed intake (FI), or the feed efficiency (FE) of an animal is provided. The method comprises feeding the animal with feed that is coated with a dispersion of lysed microbial cells in triglyceride oil wherein the lysed cells have an aspect ratio of less than 1:1. The method can increase the TGC, FI and FE of the animal.

In some embodiments, a method of decreasing the docosahexaenoic acid content in the feces of an animal is provided. The method comprises feeding the animal with feed that is coated with a dispersion of lysed microbial cells in triglyceride oil wherein the lysed cells have an aspect ratio of less than 1:1.

In some embodiments, a method of increasing the protein deposition (PD), lipid deposition (LD), docosahexaenoic deposition (DHAD), or the eicosapentaenoic acid (EPAD) of an animal is provided. The method comprises feeding the animal with feed that is coated with a dispersion of lysed microbial cells in triglyceride oil wherein the lysed cells have an aspect ratio of less than 1:1. The method can increase the PD, LD, DHAD, or EPAD of the animal.

DESCRIPTION

Definitions

Figure 1:
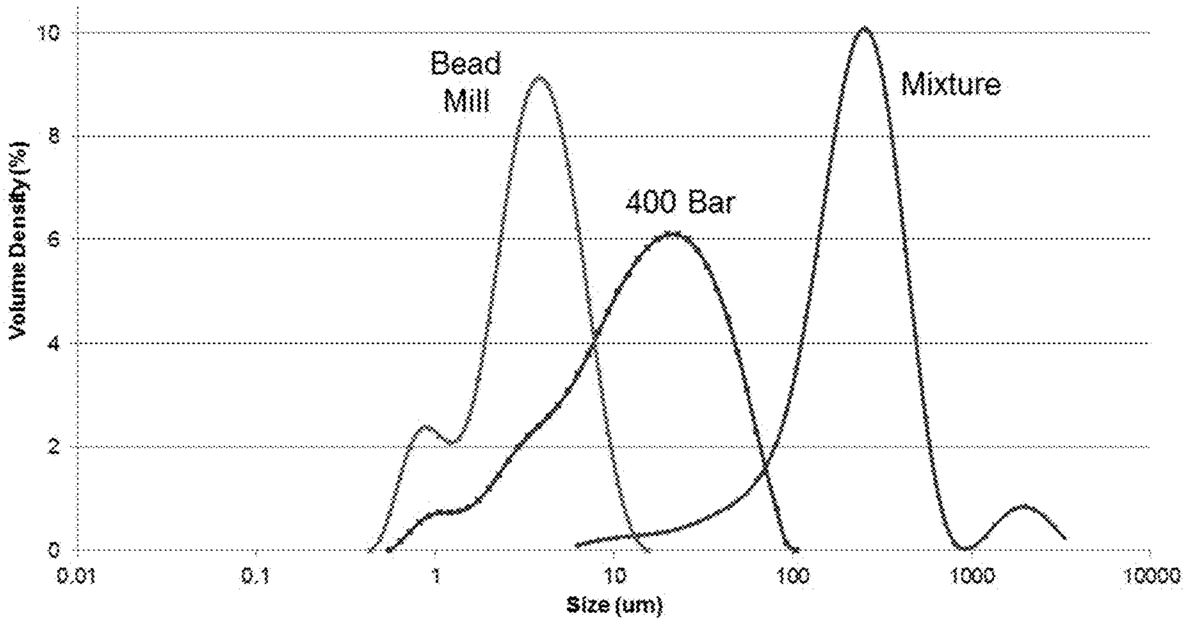
FIG. 1 shows the percent volume density as a function of particle size (μm) for the canola oil and biomass mixture of Example 2 and of the dispersions resulting from subsequent homogenization or bead milling of the mixture.

"Aspect ratio" refers to the ratio of the width to the height of the lysed cell or unlysed cell.

"Dietary addition(s)" are ingredients that are added to feed ingredients to provide micronutrients or other compounds to enhance yield or the quality of the animal product. Dietary additions are typically oil soluble compounds but can be water soluble compounds. Dietary additions include but are not limited to astaxanthins, carotenoids, flavonoids, sterols, chalcitriols (Vitamin D), tocopherols (vitamin E), and phylloquinone and menaquinone (vitamin K). Astaxanthins are used in aquaculture to enhance the color of products such a salmon and trout. Other dietary additions include antibiotics, antifungals, and antiparasitics used to protect the health of the animal and hormones to increase the growth rate and size of the animal. The feed ingredient composition can further comprise yeast, bacteria, fungi, microalgae or other microorganisms that produce astaxanthins, carotenoids and other micronutrients.

"Dispersion" refers to solid in oil mixtures. In such mixtures the solids are visibly present to the naked eye without the aid of magnification.

A "fatty acid profile" is the distribution of fatty acyl groups in the triglycerides of the oil without reference to attachment to a glycerol backbone. Fatty acid profiles are typically determined by conversion to a fatty acid methyl ester (FAME), followed by gas chromatography (GC) analysis with flame ionization detection (FID). The fatty acid profile can be expressed as one or more percent of a fatty acid in the total fatty acid signal determined from the area under the curve for that fatty acid. FAME-GC-FID measurement approximate weight percentages of the fatty acids.

"Fatty acid" in the context of a triglyceride oil refers to the fatty acyl moieties in a triglyceride. Accordingly it will be understood that fatty acyl groups of triglycerides can be described in terms of the carboxylic acid is produced when the triglyceride is hydrolyzed or saponified.

"Feed ingredient" refers to substances that are added to other ingredients or foods to make or modify a food.

"Feed efficiency" (FE) is the gain in body mass (weight) per given amount of feed consumed by the animal.

"Feed intake" (FI) is the amount of feed consumed by an animal during a defined period of time.

"Food", "edible food", "feeds", "formulated feed" and "finished food products" refer to products having some nutritional value suitable for ingestion by a living organism.

"Lipid deposition" (LD) is the increase in the lipid content of the animal in degree days (mg ° C./day). The efficiency of lipid deposition (eLD) is the percentage of lipids that is fed to the animal that ends up in the lipid content of the animal. "Docosahexanenoic acid deposition" (DHAD) is the increase in the DHA content of the animal in degree days (mg ° C./day). The efficiency of "docosahexaenoic acid deposition" (eDHAD) is the percentage of docosahexaenoic acid that is fed to the animal that ends up in the DHA content of the animal. "Eicospentaenoic acid deposition" (EPAD) is the increase in the EPA content of the animal in degree days (mg ° C./day). The efficiency of "eicosapentaenoic acid deposition" (eEPAD) is the percentage of eicosapentaenoic acid that is fed to the animal that ends up in the lipid content of the animal.

"Low chloride" refers to growth conditions in which the amount of chloride is lower than the salinity of marine environments.

"Lyse," "Lysing," "lysis," means disrupting or disruption the cell wall or cellular membrane of a cell sufficient to release at least some intracellular content.

"Lysed" cells or "disrupted" cells are those where the cellular wall and/or membrane have been disrupted. After lysis, the cell's contents, including triglyceride oil, is partially or wholly released from the cell. After disruption of the cellular wall and/or membrane, some portion of the intracellular contents, including triglyceride oils may remain inside the disrupted cell wall or membrane.

"Microbial cell" refers to a unicellular microorganism. Unicellular microorganisms include eukaryotic microbial organisms. Microbial organisms include those capable of photosynthesis as well as heterotrophs, which can live solely off of a fixed carbon source.

An "oleaginous" cell, microbe, or microrganism is capable of producing at least 20% lipid by dry cell weight, naturally or through recombinant or classical strain improvement. Oleaginous cells and microorganisms include those such as microalgae, fungus, and yeast.

"Protein deposition" (PD) is the increase in the protein content of the animal in degree days (mg ° C./day). The efficiency of protein deposition (ePD) is the percentage of protein that is fed to the animal that ends up in the protein content of the animal.

A "slurry" or "microalgal slurry" is a dispersion of lysed microbial cells in triglyceride oil. The slurry comprises lysed microlagal cells with an aspect ratio of less than 1:1. The slurry can be top coated, vacum coated, spray coated onto solid feed. The solid feed can be prepared by pelleting, extruding, forming or prepared by using other known methods of preparing solid feed.

A "thermal unit growth coefficient" (TGC) is a mathemical coefficient that that describes the grown of aquatic species that accounts for changes in growht pattern occurring across the life stages of the animal.

"Triglyceride molecule" refers to a single triglyceride composed of three fatty acids that are attached to a glycerol backbone as esters. "Triglycerides oils" refer to a collection of varying triglyceride molecules that differ in the nature and proportion of the different fatty acids and in how the different fatty acids are attached to the glycerol backbone relative to one another.

In some embodiments, the microbial cells contain triglyceride oils rich in DHA. Commercial sources of DHA rich oils are obtained from the species from the genus *Schizochytrium*, with sp. denoting that the species is unidentified. Such cells can be prepared by heterotrophic fermentation as described by Barclay in U.S. Pat. Nos. 5,130,242, 5,340,742, and 5,340,594.

Most commercial processes to produce DHA cells involve the use of a defined culture medium, industrial aerobic fermentation vessels, defined operating parameters (such as pH/temperature/salt levels), and double drum driers to produce the characteristic fine-flake powder.

Sea water contains about 0.55 M chloride. Chloride ions cause corrosion of stainless steel equipment in industrial settings. It is advantageous to minimize the amount of chloride in fermentation media and other liquids used during cultivation and processing to minimize corrosion. Marine organisms that have been adapted to grow in conditions with chloride concentrations of less than 0.55 M are provided herein. The low chloride conditions of the invention are 300 to 500 mM chloride, 100 to 300 mM chloride, 50 to 100 mM chloride, 1 to 75 mM chloride, 1 to 50 mM chloride, 1 to 40 mM chloride, 1 to 30 mM chloride, 1 to 20 mM chloride, 1 to 15 mM chloride, 1 to 10 mM chloride, 0.5 to 10 mM chloride, 0.5 to 7.5 mM chloride, or 0.5 to 5 mM chloride.

Drying of the microbial cells in the aqueous fermentation broth can be accomplished by first optionally dewatering fermentation broth (concentrating the fermentation broth) to increase the cellular content of the broth. Dewatering or concentrating refers to the separation of the biomass from fermentation broth or other liquid medium and so is solid-liquid separation. Thus, during dewatering, the culture medium is removed from the biomass (for example, by draining the fermentation broth through a filter that retains the biomass), or the biomass is otherwise removed from the culture medium. Common processes for dewatering include centrifugation, filtration, and the use of mechanical pressure. These processes can be used individually or in any combination.

After the optional dewatering step, the concentrated broth, now with a higher solids content, can be dried by know drying methods, including but not limited to drum drying, pneumatic drying, spray drying, lyophilizing and other drying methods.

A drum dryer operates by applying a film of the fermentation broth (or dewatered fermentation broth) to the surface of a rolling, heated drum. The aqueous portion of the broth evaporates leaving a dried solid on the surface of the drum. The dried solids are then scraped off the drum with a knife. Pneumatic dryers draw or entrain the material that is to be dried in a stream of hot air. While the material is entrained in the hot air, the moisture is rapidly removed. The dried material is then separated from the moist air and the moist air is then recirculated for further drying. A spray dryer operates by spraying the fermentation broth (or dewatered fermentation broth) in a fine droplet dispersion into a current of heated air. The entrained material is rapidly dried and forms a dry powder. Spray drying can be accomplished by a box-dryer, or a tall-form spray-dryer, a fluidized bed dryer, or a moving fluidized bed dryer (e.g., a FilterMat® spray dryer, GEA Process Engineering, Inc.).

The dried powders can be mixed with oils that have been extracted from other organisms. The oils can be neat oils that are substantially free from solid materials. The oils can be oils extracted such as from plant oils, fish oils, or combinations thereof. The oils are predominantly triglyceride oils. Fish oils rich in DHA include the oils from wild anchovies from South American and herring from the Northern hemisphere. Oils mixed with the dried powders can also include oil extracted from thraustochytrids. In some cases where the oils are predominantly oils from plants and contain less than 50%, 40%, 30%, 20%, or 10% fish oil.

The mixed powders and oils can be milled or other methods used to lyse the microbial cells. Lysing the cells allow triglyceride oil from the cells to be released into the feed ingredient composition. Mechanical lysing can be performed by various well known methods such as by roller mill, homgenizer, or bead milling.

The extent of cell disruption can be ascertained by microscopic analysis. The percent of the lysed cells can be determined by observing and counting the number of lysed and unlysed cells after lysis of the cells. In specific embodiments, the lysed cells of the invention are greater than 50%, 60%, 70%, 80%, 90%, or 95% lysed.

Lysis or disruption of cells may be accomplished by mechanical, enzymatic, chemical, viral, electrical, ultrasonic, osmotic or other methods. A pressure disruptor, such as a high pressure homogenizer can be used to lyse the cells. A pressure disrupter lyses cells by pumping a mixture of cells and oil, e.g., canola oil or other plant oil, through a restricted orifice valve to lyse the cells. High pressure (from 50 bar up to 1500 bar) is applied, followed by an instant expansion through an exiting nozzle. A Niro (Niro Soavi GEA) homogenizer (or any other high pressure homogenizer) or other commercially available homogenizer can be used to process cells to particles of 5 to 500 micrometers in length. The aspect ratio of the lysed cells decrease from a value of about 1:1 for unlysed cells to 1:1, 1:2, 1:3, 1:4, 1:5, 1:6, 1:7, 1:8, 1:9 or 1:10. Processing of biomass with high pressure homogenizers can produce lyses of the cells to over 50%, 60%, 70%, 80%, 90%, 95% or greater than 95% of the cells by controlling the pressure, exit velocity and other parameters.

Alternatively, a ball mill (also known as a bead mill) can be used. In a ball mill, cells are agitated in suspension with small abrasive particles, such as beads. Cells break because of shear forces, grinding between beads, and collisions with beads. The beads disrupt the cells to release cellular contents. Dyno-mill ECM Ultra (CB Mills) ball mill and other commercially available bead mills can be used. Cells can also be disrupted by shear forces, such as with the use of blending (such as with a high speed or Waring blender as examples), the french press, or even centrifugation to disrupt cells. Shear mixers can be used to lyse cells, including in-line high shear mixers and bulk high shear mixers.

The aspect ratio of the lysed cell is less than 1:1. In another embodiment the aspect ratio is 1:2, 1:3, 1:4, 1:5, 1:6, 1:7, 1:8, 1:9 or 1:10. The aspect ratio of the unlysed cell is approximately 1:1. One advantage of lysed cells is that they have an aspect ratio of less than 1:1. The smaller aspect ratio is advantageous because as the lysed cell/oil slurry is used in industrial equipment, the lysed cell/oil slurry prevents or minimizes clogging of the equipment, including orifices that are used to spray the lysed cell/oil slurry onto extruded feed.

The feed ingredient composition can then be formulated with other feed ingredients to produce a formulated feed. In some embodiments feed ingredient composition containing lysed cells is coated onto pressed or extruded feed such as by spraying. The pressed or extruded feed can be high in protein such as those derived from fish and/or animal by-products. The formulated feed can also include additional additives to improve flavor, stability, and shelf-life.

The formulated feed can be used in aquaculture to feed farmed fish or shell fish. Farmed fish include carnivorous fish. In some embodiments the farmed fish or shell fish are salmonids, eels, crustaceans, marine fish, fresh water fish, tilapia, or eels. In other embodiments the fish or shell fish is a sea bass, sea brim, yellow tail, grouper, barramundi, or shrimp.

EXAMPLES

Example 1. Food Ingredient

DHA rich *Schizochytrium* cells (biomass) prepared by standard heterotrophic fermentation were dried and blended using a standard impeller type mixer with canola oil at loading levels of 10%, 20%, and 30% by weight biomass. The biomass in oil blends were then processed through either a high pressure homogenizer or a bead mill to yield a dispersion of lysed algal cells in oil. For lysis in the high pressure homogenizer, pressures from 200 to 1200 bar were utilized and were sufficient to lyse the cells.

Example 2. Analysis of Mixture and Dispersions Prepared from the Mixture

A 20% by weight biomass blend with canola oil of Example 1 was prepared and analyzed by laser diffraction particle size analysis on a Malvern Mastersizer 3000. The mixture was also homogenized at 400 bar and bead milled, and the resulting dispersions were also analyzed. FIG. 1 shows that the bead milled dispersions had a lower average particle size than the homogenized dispersions, and both had lower average particle sizes than the parent mixture.

Figure 2:
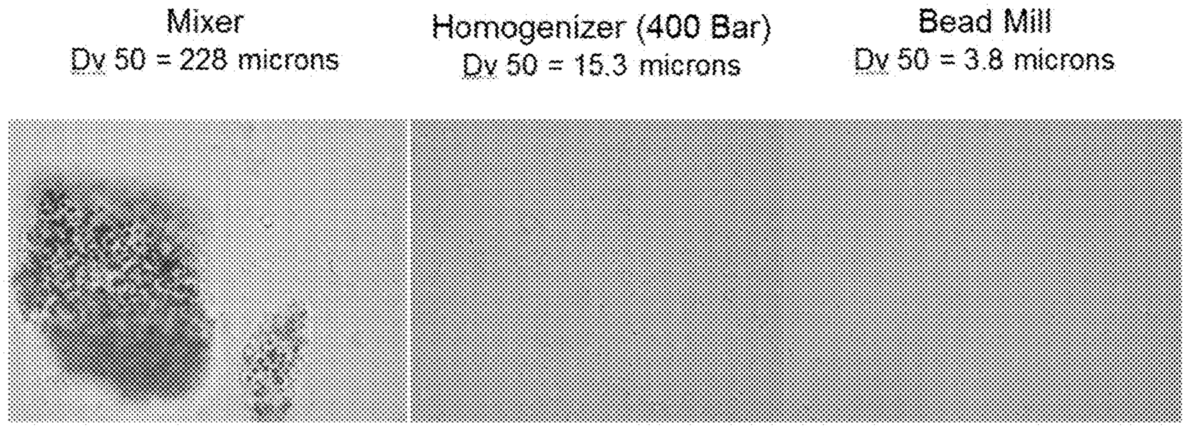
FIG. 2 shows micrographs of the mixture and of the dispersions of Example 2.

The smaller sizes are also seen in the micrographs of FIG. 2 (400× magnification). The Dv50 value (distribution value of 50% or less) of the mixture was 228 μm, while the homogenized dispersion had a Dv50 of 15.3 μm and the bead milled dispersions had a Dv50 of 3.8 μm, indicating that the dispersions have better characteristics for use in sprayers.

Figure 3:
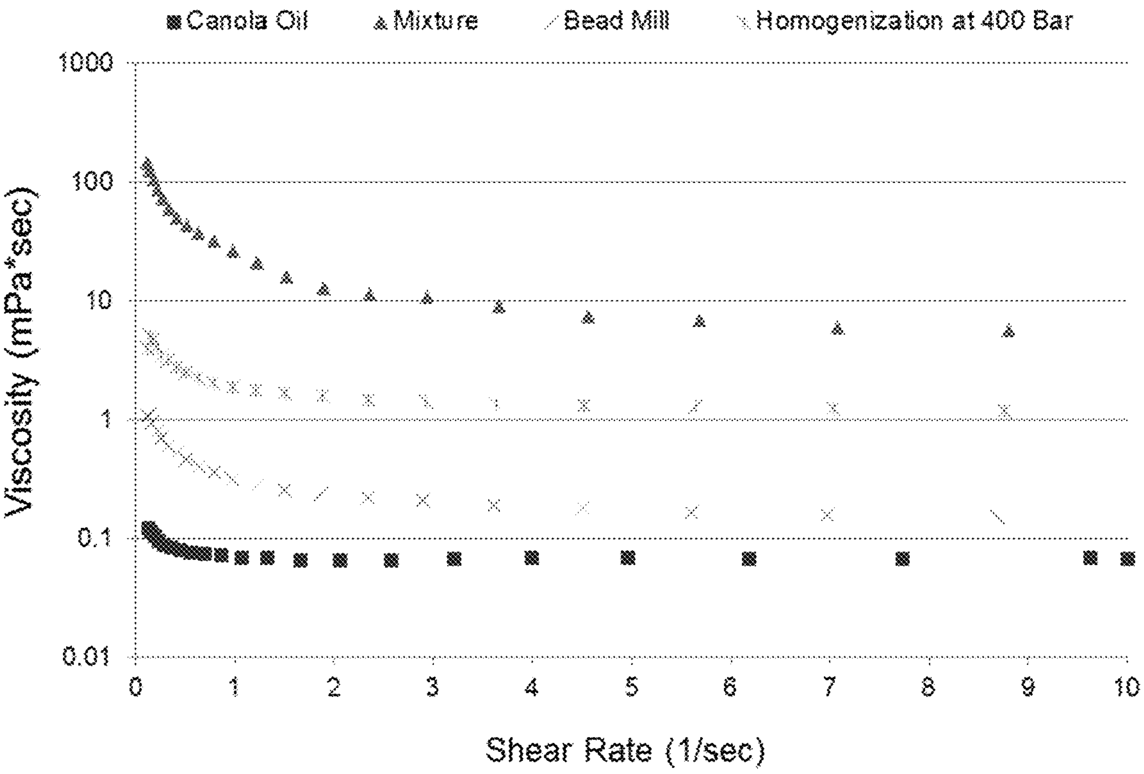
FIG. 3 shows the viscosity as a function of shear rate of the mixture and of the dispersions of Example 2.

A Malvern Kinexus Pro Rheometer was used to measure the viscosity of FIG. 3. The bead milled dispersions were found to have a lower viscosity at any given shear rate compared to the homogenized dispersions, which in turn was lower than the mixture.

Figure 4:
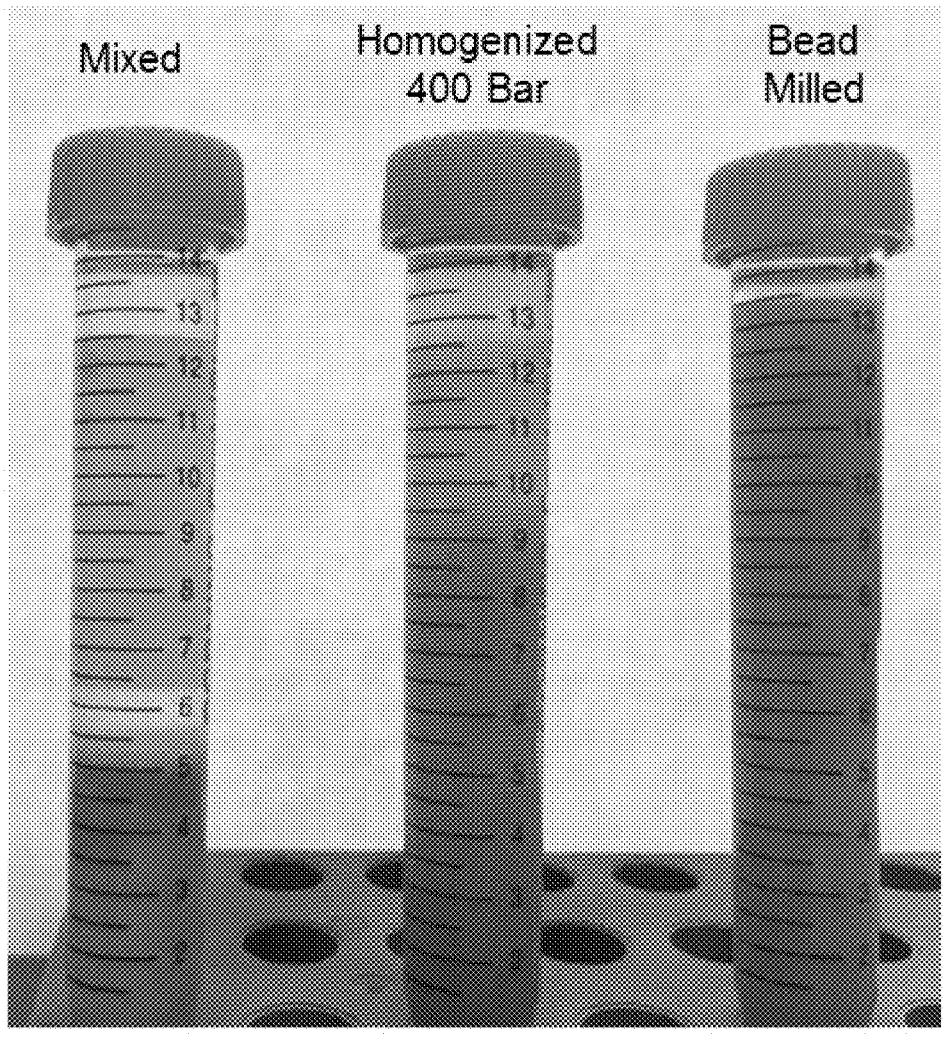
FIG. 4 shows the appearance of the mixture and of the dispersions of Example 2 after 1 week.

The mixture and the two dispersions were allowed to settle and their appearances after one week are shown in FIG. 4. The bead milled dispersion was found to remain substantially in suspension. The mixture showed the greatest degree of settling.

Example 3. Analysis of Oxidative Stability

Figure 5:
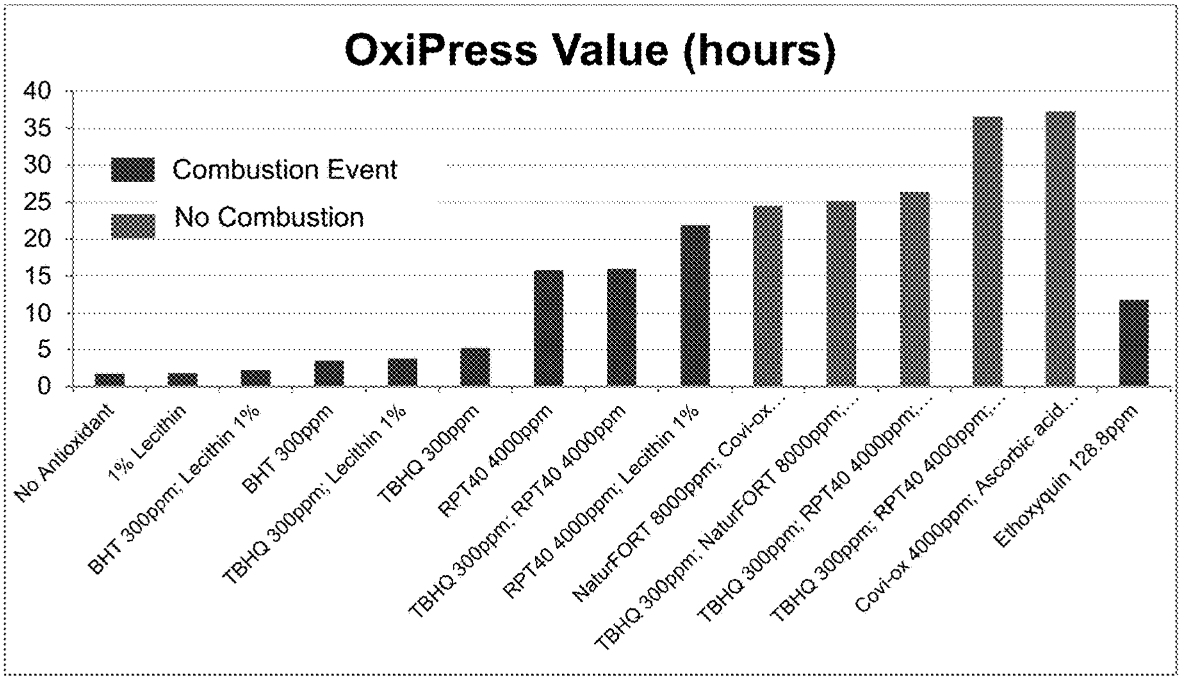
FIG. 5 shows the OxiPress values (hours) of the biomass and/or antioxidants of Example 3.

The dry biomass of Example 1 was combined with various antioxidants using a hand blender. The dry biomass with or without antioxidants were analyzed using an Oxipress at approximately 80° C. Natural and synthetic antioxidants were used and included L-alpha-Lecithin (soy, Calbiochem #429415), starch (corn, Argo), ascorbic acid (Spectrum Chemical Co.), ParadigmOx White Liquid (PWL-gallates, Kemin), RPT40 (rosemary, tocopherol, ascorbyl palmitate, Kemin), NaturFort LGR105 (green tea and rosemary extracts, Kemin), Rendox CQ (TBHQ, Kemin), Rendox EQ (ethoxyquin, Kemin) BHT (crystalline dissolved in ethanol, Kemin), and Covi-ox T-30P (mixed tocopherols). FIG. 5 shows the surprising and unexpected oxidative stability of certain lecithin containing biomass.

The oxidative stability of the biomass when prepared with antioxidants RPT40 (4,000 ppm) and lecithin (1%) is approximately 22 hours at 80° C. This is surprising and unexpected because the oxidative stability of the biomass when formulated with 4,000 ppm RPT40 alone is about 16 hours and the oxidative stability of the biomass when formulated with 1% lecithin alone is about 1.5 hours. When the biomass is formulated with both RPT40 and lecithin, the stability is 22 hours, far higher than the predicted stability of 17.5 hours.

Example 4. Formulated Feed

The slurry of Example 1 was top coated onto extruded feed pellets using a vacuum coating apparatus. The resulting pellet contained 20% by weight of the dispersion of Example 1.

Example 5. Salmonid Feeding Study

Four aquaculture diets were formulated to contain 2.0% DHA and a DHA to EPA ratio between 2.1 and 2.5. Table 1 below discloses the ingredients and the amounts of each ingredient for diets A, B, C, and D. Table 2 below discloses the nutritional content of the four diets. Diet A (Control) contained no *Schizochytrium* biomass, but used standard fish oil applied as a topcoat as the main dietary source of DHA (besides fishmeal that contains low levels of DHA). Diet B contained unlysed *Schizochytrium* biomass. For diet B, after the feed was extruded, the pellets were top coated with canola oil and herring oil. Diet C contained bead milled *Schizochytrium* biomass that was mixed with canola oil and vacuum coated along with the other oils shown in Table 1 on extruded salmon feed. Diet D contained *Schizochytrium* biomass that was homogenized at 400 bar and mixed with canola oil and vacuum coated along with the other oils shown in Table 1 on extruded salmon feed. DHA levels ended up being lower than expected at ~1.5% instead of 2%. This discrepancy between calculated and observed dietary DHA contents may have resulted from DHA levels lower than usual in one of the fish oils. Table 2 shows the nutritional content of the diets A, B, C and D. The herring oil was purchased and typical fatty acid content of herring oil can be found at NRC (2011). The Fish oil Tuna 70DHA ingredient is commercially available from Edwards International Inc.

TABLE 1

Feed formulas (calculated) of the experimental diets

| IM Code | Ingredients | A (control) | B (AP) | C (AP-BM) | D (AP-H400) |
|---|---|---|---|---|---|
| 55 | Dicalcium phosphate (40% P205) | 4.056 | 4.000 | 4.019 | 4.019 |
| 59 | Biolys | 1.500 | 1.343 | 1.340 | 1.340 |
| 60 | DL Methionine | 0.274 | 0.000 | 0.111 | 0.111 |
| 300 | Fish oil herring | 9.198 | 8.878 | 1.000 | 1.000 |
| 302 | Fish oil tuna 70DHA | 1.886 | 0.000 | 1.038 | 1.038 |
| 304 | Fish oil herring_Schizo | 0.000 | 0.000 | 10.907 | 10.907 |
| 310 | Canola oil | 12.005 | 9.783 | 10.595 | 10.595 |
| 320 | Vit & Min Premix | 0.200 | 0.200 | 0.200 | 0.200 |
| 330 | Carophyll Pink | 0.050 | 0.050 | 0.050 | 0.050 |
| 500 | Fishmeal Herring | 5.000 | 5.000 | 5.000 | 5.000 |
| 510 | Poultry by-product mean (Low ash) | 16.565 | 20.000 | 17.796 | 17.796 |

TABLE 1-continued

| Feed formulas (calculated) of the experimental diets | | | | | |
|---|---|---|---|---|---|
| IM Code | Ingredients | A (control) | B (AP) | C (AP-BM) | D (AP-H400) |
| 550 | Soy protein concentrate | 10.000 | 6.802 | 8.876 | 8.876 |
| 561 | Corn Protein concentrate | 20.000 | 20.000 | 20.000 | 20.000 |
| 565 | Wheat gluten meal | 10.000 | 9.671 | 10.000 | 10.000 |
| 567 | Wheat Flour | 9.266 | 9.274 | 9.067 | 9.067 |
| 572 | AlgaPrime (AP) | 0.000 | 5.000 | 0.000 | 0.000 |

TABLE 2

| Calculated Nutritional content of the experimental diets | | | | | | |
|---|---|---|---|---|---|---|
| CH Code | Nutrient | Content | | | | Unit |
| 1 | Percent Mass | 100.000 | 100.000 | 100.000 | 100.000 | % |
| 2 | Dry matter | 92.745 | 92.598 | 92.515 | 92.515 | % |
| 3 | Crude Lipid | 28.000 | 27.276 | 28.000 | 28.000 | % |
| 5 | Crude protein | 46.000 | 46.000 | 46.000 | 46.000 | % |

TABLE 2-continued

| Calculated Nutritional content of the experimental diets | | | | | | |
|---|---|---|---|---|---|---|
| CH Code | Nutrient | Content | | | | Unit |
| 6 | Crude fiber | 0.850 | 0.775 | 0.797 | 0.797 | % |
| 7 | Ash | 5.396 | 5.910 | 5.457 | 5.457 | % |
| 11 | Calcium | 1.129 | 1.114 | 1.119 | 1.119 | % |
| 12 | Phosphorus | 1.017 | 1.018 | 1.006 | 1.006 | % |
| 13 | Digestible phosphorus | 0.670 | 0.670 | 0.670 | 0.670 | % |
| 74 | Leucine | 4.661 | 4.659 | 4.654 | 4.654 | % |
| 75 | Isoleucine | 1.904 | 1.898 | 1.899 | 1.899 | % |
| 77 | Phenylalanine | 2.163 | 2.120 | 2.145 | 2.145 | % |
| 84 | Histidine | 0.974 | 0.968 | 0.970 | 0.970 | % |
| 85 | Arginine | 2.401 | 2.438 | 2.408 | 2.408 | % |
| 103 | Vitamin E | 1.825 | 1.848 | 1.834 | 1.834 | mg/kg |
| 800 | Digestible lysine | 2.590 | 2.500 | 2.500 | 2.500 | % |
| 801 | Digestible methionine | 1.056 | 0.813 | 0.900 | 0.900 | % |
| 802 | Lysine | 2.907 | 2.816 | 2.816 | 2.816 | % |
| 803 | Methionine | 1.187 | 0.948 | 1.031 | 1.031 | % |
| 820 | Gross energy | 24.894 | 24.512 | 24.722 | 24.722 | MJ/kg |
| 821 | Digestible energy | 21.188 | 20.868 | 21.040 | 21.040 | MJ/kg |
| 830 | Astazanthin | 0.005 | 0.005 | 0.005 | 0.005 | % |
| 840 | DHA | 2.000 | 2.000 | 2.000 | 2.000 | % |
| 841 | EPA | 0.951 | 0.804 | 0.800 | 0.800 | % |
| 843 | n3-Total | 4.801 | 2.765 | 4.304 | 4.304 | % |
| 844 | n6-Total | 2.581 | 2.127 | 2.340 | 2.340 | % |
| 845 | n3:n6 Ratio | 1.860 | 1.300 | 1.840 | 1.840 | |
| 846 | DHS:EPA Ratio | 2.103 | 2.487 | 2.500 | 2.500 | |

Table 3 shows the comparison between calculated (Cal.) and analysed nutrient composition of experimental diets. In Table 3, AVC and NJFL refer to the laboratories where analyses were conducted. The analysed crude protein in experimental diets was 2-4% higher than calculated. In contrast, the analysed dietary crude lipid, DHA and EPA were lower than the calculated ones. Slight differences were also observed between laboratories;

Differences between calculated and analysed nutrients can be explained by the composition of ingredients that differ sometimes from one batch to the other as well as from the composition prescribed in the formulation software and uncertainties of analytical methods.

TABLE 3

| comparison between calculated (Cal.) and analysed nutrient composition | | | | | | | | | | | | |
|---|---|---|---|---|---|---|---|---|---|---|---|---|
| | Crude protein (% as-is) | | | Crude lipid (% as-is) | | | DHA (% as-is) | | | EPA (% as-is) | | |
| Diet | Cal. | AVC | NJFL | Cal. | AVC | NJFL | Cal. | AVC | NJFL | Cal. | AVC | NJFL |
| A (Control) | 46.0 | 50.4 | 49.0 | 28.0 | 23.2 | 23.3 | 2.00 | 1.22 | 1.11 | 0.95 | 0.53 | 0.47 |
| B (AP) | 46.0 | 49.5 | 48.4 | 27.3 | 24.3 | 25.3 | 2.00 | 1.52 | 1.19 | 0.80 | 0.47 | 0.43 |
| C (AP-BM) | 46.0 | 50.0 | 49.2 | 28.0 | 26.2 | 23.7 | 2.00 | 1.56 | 1.30 | 0.80 | 0.63 | 0.54 |
| D (AP-H400) | 46.0 | 49.6 | 49.1 | 28.0 | 24.3 | 23.6 | 2.00 | 1.48 | 1.38 | 0.80 | 0.58 | 0.54 |

Rearing conditions: Salt water in a recirculating aquaculture system equipped with eight 850-liter circular tanks. The water was maintained at 13.7±1.3° C. and >80% saturation of dissolved oxygen. Each experimental diet was allocated randomly to two tanks.

Sample collection: Fillets on nine fish (pooled) at the start and three fish from each tank at days 28, 56, 84 and 112 were prepared. The Fillets corresponded to Trim E at http://primanor.com/salmon-fillet-trim-guide/, i.e. skinless, trimmed with no belly fat, fins off. The only exception was that the pin bones were not removed. Fecal matter, pooled per treatment group, were collected at day 84 and 112.

Laboratory analysis: Proximate analyses of protein, lipid, ash, dry matter and total fatty acid composition of diets (n=4), feces (n=8) and fillets on three fish per tank pooled per tank (n=33) were performed. Chemical analysis was conducted as follows: dry matter, 105° C. for 16 h (AOAC 930.15), ash at least 6 h at 550° C. and nitrogen (AOAC 990.03; using a 78-elemental analyzer LECO FP528, St. Joseph, Mich., USA; crude protein=N×6.25), and lipid (Bligh & Dyer, 1959). The total fatty acid contents of diets and fillets were determined according to McNiven et al. (2011). Briefly, fatty acid methyl esters (FAME) were prepared according to the procedure of Sukhija and Palmquist (1988) and were analyzed on a Hewlett Packard 5890 gas liquid chromatograph fitted with a 7673 series auto-sampler and injector, Agilent DB23 fused silica capillary column (30 m×0.53 mm id×0.5 m film thickness), FID detector, and integrated with Agilent Chemstation software (Agilent Technologies Canada Inc., Mississauga, ON, Canada). The operating conditions were: On-Column injection; oven temperature, 70° C. for 0.5 min then 10° C./min to 170° C. and held for 3 min, 5° C./min to 210° C. and held for 6 min, 25° C./min to 230° C. and held for 4.2 min; detector temperature, 250° C.; hydrogen as carrier gas and nitrogen as make up gas. Nonadecanoic acid was added as an internal standard and FAME standards (Nu-Chek-Prep, Elysian, Minn., USA; Matreya, Pleasant Gap, Pa., USA) were used to identify the chromatographic peaks. Results were reported as mg/100 mg of total fatty acid utilizing published correction factors (Ackman, 2002).

Calculations and Statistical Analysis:

Growth rate was calculated using the thermal-unit growth coefficient (TGC):

$$TGC = \left( \frac{W_f^{1/3} - W_0^{1/3}}{\sum_{i=1}^{n} T_i} \right) \times 100$$

where $W_f$ and $W_0$ are final and initial body weight, respectively, of fish in units of g, n (=1, 2, . . . ) is the day number recorded from $W_0$, and $T_i$ (° C.) is mean daily water temperature.

The results from the proximate and fatty acid analyses served to describe the rates of nutrient deposition using the following equation (Dumas et al., 2007):

$$D_j = \frac{F_j - I_j}{\sum_{i=1}^{n} (T_i \times t_i)}$$

where $D_j$ is deposition rate [mg (° C.·d)$^{-1}$] of nutrient j, $F_j$ and $I_j$ are final and initial whole-body mass of nutrient j (mg) at the end and the beginning of the 84-day period, respectively, n stands for the day number covering the period from $F_j$ to $I_j$, $T_i$ (° C.) is mean daily water temperature for day $t_i$, the product of which results in units of degree-days.

The rates of nutrient deposition served, in turn, to estimate the efficiency of nutrient deposition using the following equations modified from Dumas et al. (2007):

$$eD_j = \frac{D_j}{\sum_{i=1}^{n} (IN_j \times t_i)} \times 100$$

where $eD_j$ is efficiency (%) of nutrient$_j$ deposition [mg (fish)$^{-1}$], $IN_j$ (mg) is daily intake of nutrient j for day $t_i$.

The results were analyzed using one-way ANOVA and Tukey's multiple comparison test with JMP® version 12.0.1 (SAS Institute Inc, Cary, N.C., USA).

4.0 Results and Discussion: No statistical differences were observed between treatments for initial body weight (P=0.590), final body weight (P=0.483), TGC (P=0.387), feed intake (P=0.588) and feed efficiency (P=0.484) (Table 4). Moreover, the dietary treatments did not affect significantly feed intake and feed efficiency (P values varied between 0.44 and 0.90). growth of salmon fed diets C (AP-BM) and D (AP-H400) was superior to that of the Control and B (AP). The TGC values observed in this study are comparable with other studies conducted with the same strain of salmon (e.g. Wolters et al., 2009. These results indicated AlgaPrime inclusion in salmon diets sustained growth performance and feed conversion similarly to fish oil.

Table 4 shows the initial body weight (IBW) and final body weight (FBW) body weight, thermal-unit growth coefficient (TGC), feed intake (FI) and feed efficiency (FE) of Atlantic salmon fed diets containing either no AlgaPrime (Control), AlgaPrime meal (AP), AlgaPrime bead-milled (AP-BM) and AlgaPrime homogenized at 400 bar (AP-H400); data are means (standard deviations); means values in a column with no superscript in common differ significantly (p<0.05) based on the Tukey test (the absence of superscript indicates no difference). The final body weight of diets B, C and D when compared to salmon that were fed the control diet (without AlgaPrime). The thermal growth coefficient increased from 0.176 up to 0.193, with p<0.05.

TABLE 4

| Diet | IBW (g fish$^{-1}$) | FBW (g fish$^{-1}$) | TGC (g$^{1/3}$ fish$^{-1}$) | FI (g fish$^{-1}$) | FE (g fish$^{-1}$) |
|---|---|---|---|---|---|
| A (Control) | 542.6 (0.9) | 1,064.3 (4.9) | 0.176 (0.002) | 607.8 (9.1) | 0.86 (0.00) |
| B (AP) | 544.6 (25.0) | 1,088.2 (56.1) | 0.182 (0.004) | 585.7 (8.6) | 0.93 (0.04) |
| C (AP-BM) | 565.1 (29.7) | 1,160.2 (76.6) | 0.192 (0.007) | 656.8 (69.7) | 0.91 (0.02) |
| D (AP-H400) | 539.7 (0.6) | 1,123.5 (70.8) | 0.193 (0.018) | 619.3 (67.9) | 0.94 (0.01) |

DHA utilization and deposition: The differences observed between treatments for protein (P=0.626), lipid (P=0.185), DHA (P=0.699) and EPA (P=0.256) concentrations in the fillets of Atlantic salmon in this study are shown in Table 5. Unexpectedly, the highest content of DHA in fillets was obtained with AlgaPrime homogenized at 400 bar. The fillet composition was not significantly affected by dietary treatments in this study (Table 5). The content of protein in Atlantic salmon fillet (FP) agreed with the literature (e.g. Waagbo et al., 1993). However, more variability was observed with the lipid and fatty acids. The lipid contents of fillets (FL) were lower than those observed by Waagbo et al. (1993) and Acharya (2011), but remained within the range reported by the FAO (http://www.fao.org/wairdocs/tan/x5916e/x5916e01.htm). The content of DHA (FDHA) and EPA (FEPA) were nearly 5× and 2× higher, respectively, in this study compared to fillets of Atlantic salmon from Chile and Canada purchased at a local grocery store (Appendix 2). In contrast, the DHA+EPA level of Atlantic salmon purchased from the local grocery store were 2× higher at least than in our study (e.g. Kousoulaki et al., 2015; Sprague et al., 2016). In Kousoulaki et al. (2016), the DHA and EPA content of fillets were comparable to this study at 0.7 and 0.1%, respectively. These differences can be explained, at least partly, by the fatty acid content of dietary lipid sources and trimming of fillets that can affect lipid and fatty acid results.

Table 5 shows the protein and lipid content of the salmon fillets. Initial and final fillet protein (FP), lipid (FL), docosahexaenoic acid (FDHA) and eicosapentaenoic acid (FEPA) of Atlantic salmon fed diets containing either no AlgaPrime (Control), AlgaPrime meal (AP), AlgaPrime bead-milled (AP-BM) and AlgaPrime homogenized at 400 bar (AP-H400); data are means (standard deviations); means in a column with no superscript in common differ significantly based on the Tukey test. The initial sample is the filet of the salmon prior to initiation of the feeding study (treatment).

TABLE 5

| Diet | FP (%) | FL (%) | FDHA (%) | FEPA (%) |
|---|---|---|---|---|
| Initial sample | 23.9 | 3.26 | 0.36 | 0.16 |
| A (Control) | 22.3 (0.3) | 5.5 (0.3) | 0.50 (0.06) | 0.12 (0.02) |
| B (AP) | 22.7 (0.8) | 4.5 (0.2) | 0.47 (0.02) | 0.09 (0.00) |
| C (AP-BM) | 23.4 (1.2) | 4.8 (0.4) | 0.47 (0.05) | 0.10 (0.01) |
| D (AP-H400) | 22.6 (0.7) | 5.2 (0.5) | 0.51 (0.03) | 0.11 (0.02) |

DHA Content of Feces: The DHA content of the feces were determined. Except for Diet B (AP), the DHA content of feces was ~75× lower than in diets, suggesting that most of the dietary DHA was uptaken by the digestive tract of salmon fed the other diets (Table 6). The DHA content of feces from salmon fed Diet B (AP) was significantly higher than that from other treatments ($P<0.05$). Perhaps the availability of DHA from AP meal was lower compared to more processed AP, but this hypothesis needs to be validated. Although we did not estimate digestibility coefficients in this study, we have demonstrated in a previous trial that digestibility of DHA from AP was high at ~95% (Dumas, 2016)

Docosahexaenoic acid (DHA) contents in diets and feces of Atlantic salmon fed diets containing either no AlgaPrime (Control), AlgaPrime meal (AP), AlgaPrime bead-milled (AP-BM) and AlgaPrime homogenized at 400 bar (AP-H400) are shown in Table 6. Data are means (standard deviations); means in a column with no superscript in common differ significantly based on the Tukey test (the absence of superscript indicates no difference). The amount of DHA in the feces of salmon fed with diet B differed with $p<0.05$. Thus the DHA provided to the salmon in the form of lysed algal slurry resulted in better absorption by the salmon than when provided to the salmon as unlysed algal biomass incorporated into the dry feed.

TABLE 6

| | DHA | |
|---|---|---|
| Diet | Diet[1] | Feces |
| A (Control) | 1.22 | 0.02 (0.00)[a] |
| B (AP) | 1.52 | 0.07 (0.01)[b] |
| C (AP-BM) | 1.56 | 0.02 (0.00)[a] |
| D (AP-H400) | 1.48 | 0.02 (0.00)[a] |

[1]No replicate was conducted on the diets.

Figure 7:
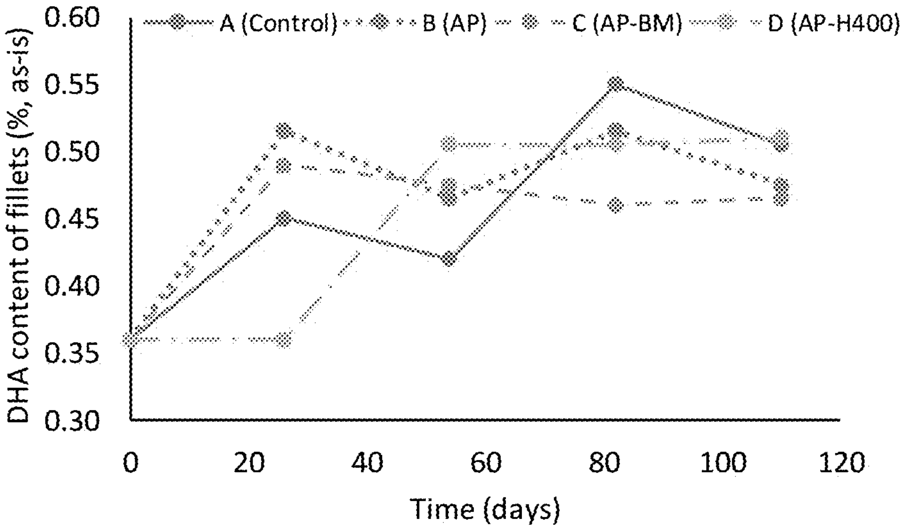
FIG. 7 shows Variations of DHA content of salmon fillets (skinless) during the study. Each data point represents the average from two samples and each sample consisted of fillets from three fish pooled per tank

The levels of DHA increased faster during the first month in fillets of salmon fed Diets B and C compared to the other treatments (FIG. 1). At day 28, the DHA contents in fillets of salmon fed Diet D were 0.27 and 0.45% in samples 1 and 2, respectively. The 0.27% sample can be considered as an outlier. In this case, the DHA content in fillets would be identical between Diet D and the Control. Overall, the highest DHA levels were achieved between one and two months into the study, and levels remained relatively similar afterwards for salmon fed with AP-containing diets. See FIG. 7

Protein, DHA and EPA deposition: The rates of protein, DHA and EPA deposition in the fillets of Atlantic salmon increased when compared to fish fed fish oil (Table 7). The p-values of the rates of protein, DHA and EPA deposition were P=0.417, P=0.639, and P=0.197, respectively. The highest deposition rates of DHA was observed with AlgaPrime homogenized at 400 bar, which is consistent with the highest DHA content reported in fillets of salmon fed the same treatment (Table 5 above). The lowest DHA deposition was recorded with Diet B (AP), which also resulted in feces containing the highest DHA content as reported at Table 6. It is thus reasonable to conclude that DHA from AP meal (Diet B) was less available. Lipid deposition (LD) was lower in fillets of salmon fed the AlgaPrime meal (Diet B) than the Control (fish oil) and AlgaPrime processed at 400 bar (Table 7). This difference could be explained by a lower lipid digestibility in AlgaPrime meal compared to homogenized AlgaPrime.

Deposition rates of protein (PD), lipid (LD), docosahexaenoic acid (DHAD) and eicosapentaenoic acid (EPAD) in fillets (skinless, trimmed) of Atlantic salmon fed diets containing either no AlgaPrime (Control), AlgaPrime meal (AP), AlgaPrime bead-milled (AP-BM) and AlgaPrime homogenized at 400 bar (AP-H400) are shown in Table 7. Data are means (standard deviations); means in a column with no superscript in common differ significantly based on the Tukey test (the absence of superscript indicates no difference). AlgaPrime, homogenized and non-homogenized, both increased the protein deposition in salmon. In addition the amount of docosahexaenoic acid and eicosapentaenoic acid deposition increased with homogenized algal biomass. Lipid deposition (LD) was significantly lower (P=0.024) in fillets of salmon fed the AlgaPrime meal (Diet B) than the Control (fish oil) and AlgaPrime processed at 400 bar (Table 5). This difference could be explained by a lower lipid digestibility in AlgaPrime meal compared to homogenized AlgaPrime. Thus the inclusion of algal cells in salmon diets as a slurry that is coated onto extruded pellets significantly increases the lipid deposition when compared to direct inclusion of algal cells in aquaculture feed.

TABLE 7

| Diet | PD (mg ° C.-d$^{-1}$) | LD (mg ° C.-d$^{-1}$) | DHAD (mg ° C.-d$^{-1}$) | EPAD (mg ° C.-d$^{-1}$) |
|---|---|---|---|---|
| A (Control) | 43.0 (0.6) | 16.0 (1.3)[a] | 1.36 (0.26) | 0.23 (0.06) |
| B (AP) | 46.6 (6.0) | 12.3 (0.3)[b] | 1.28 (0.16) | 0.11 (0.01) |
| C (AP-BM) | 54.5 (9.8) | 14.9 (0.6)[a,b] | 1.33 (0.13) | 0.19 (0.05) |
| D (AP-H400) | 49.6 (3.0) | 16.1 (0.8)[a] | 1.50 (0.02) | 0.23 (0.06) |

Figure 6:
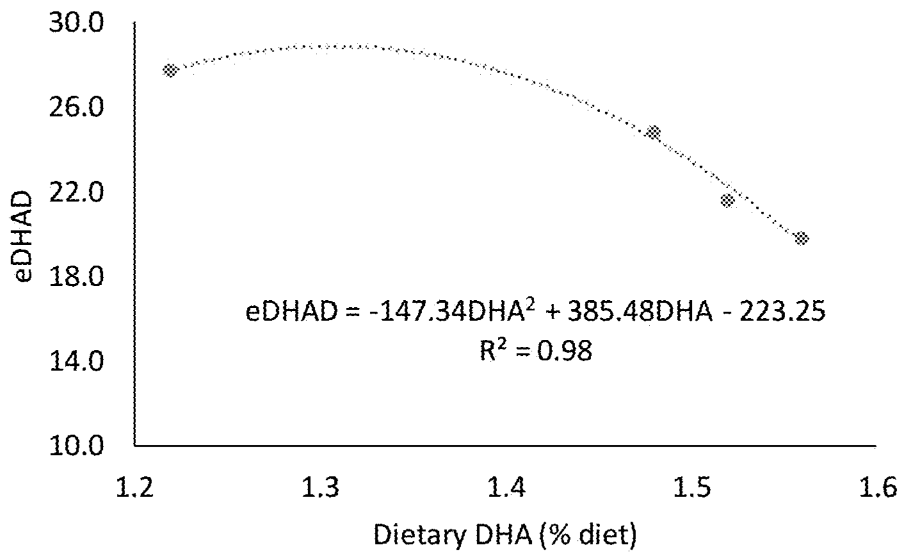
FIG. 6 shows the relationship between dietary DHA levels and efficiency of DHA deposition (eDHAD) of Example 5.

AlgaPrime and fish oil resulted in higher efficiencies of protein (P=0.397), lipid (P=0.205), DHA (P=0.239) and EPA (P=0.371) deposition (Table 8). Efficiency of DHA deposition (eDHAD) is inversely related to dietary DHA content/availability (Roselund et al., 2016; Kousoulaki et al., 2016). The results disclosed herein corroborated this observation (FIG. 6). Therefore, low eDHAD values can be explained by high levels of available DHA in the diet and does not necessarily mean that one source of DHA is better than another. Efficiencies of nutrient deposition were calculated using the laboratory results from AVC reported in Table 3.

Table 8 shows the efficiency of protein (ePD), lipid (eLD), docosahexaenoic acid (eDHAD) and eicosapentaenoic acid (eEPAD) deposition in fillets (skinless, trimmed) of Atlantic salmon fed diets containing either no AlgaPrime (Control), AlgaPrime meal (AP), AlgaPrime bead-milled (AP-BM) and AlgaPrime homogenized at 400 bar (AP-H400). Data are means (standard deviations); means in a column with no superscript in common differ significantly based on the Tukey test (the absence of superscript indicates no difference). AlgaPrime, homogenized and non-homogenized, both increased the efficiency of protein deposition. The efficiency of lipid deposition increased with homogenized algal biomass. In addition the efficiency of eicosapentaenoic acid deposition increased with homogenized algal biomass.

TABLE 8

| Diet | ePD (%) | eLD (%) | eDHAD (%) | eEPAD (%) |
|---|---|---|---|---|
| A (Control) | 21.1 (0.6) | 17.1 (1.6) | 27.7 (5.7) | 10.7 (2.8) |
| B (AP) | 24.2 (2.8) | 13.0 (0.5) | 21.6 (2.4) | 5.9 (0.3) |
| C (AP-BM) | 24.9 (1.9) | 13.2 (1.9) | 19.8 (4.0) | 7.0 (1.1) |
| D (AP-H400) | 24.4 (1.2) | 16.3 (2.6) | 24.9 (2.5) | 9.9 (3.7) |

Example 6. Low-Chloride Tolerant Strains of *Schizochytrium Limacinum*

The presence of high levels of chloride poses corrosion challenges in industrial equipment including fermentation tanks, piping, pumps, and other units. The reduction of chloride provides benefits of lower corrosion potential in equipment used for the cultivation and processing of DHA-rich biomass.

*Schizochytrium* cultures were serially cultivated in reduced chloride medium until the population evolved and was able to achieve growth similar to that of the parent strain in the original full chloride medium. The evolved population was screened for isolates to identify strains suitable for cultivation in media with reduced chloride levels

*S. limacinum* strain, S9026, was used as the source culture for the evolution of tolerance to low chloride. Growth in these cultivations was monitored as Optical Density (OD) by measuring absorbance at 750 nm. Cells (1.5 mL) of S9026 that had been cryopreserved with 20% (w/v) glycerol at −80° C. were thawed at ambient temperature and used to inoculate 50 mL of O3SF25 medium which contains 8.4 mM chloride (Table 9 and 10) in a 250-mL baffled flask. This cell culture was then incubated at 28° C. and 200 rpm on a rotary shaker with a 2-inch stroke for 24 h, until the $OD_{750}$ ranged from 3-6. 5% of the resulting primary seed culture was used to inoculate 50 ml of modified O3SF25 medium with 0.25 mM chloride (97% reduction in chloride) in a 250-mL baffled flask. The reduced chloride culture was incubated at 28° C. and 200 rpm on a rotary shaker until its final $OD_{750}$ reached 3-6. In contrast to the primary culture of S9026 which achieved the target growth within 24 hrs, the reduced chloride cultivation required 4-5 days to achieve the target growth indicating the requirement for chloride by S9026. The resulting cell culture was serially sub-cultured 4 times into modified O3SF25 medium with 0.25 mM chloride in a 250-mL baffled flask until its cell growth rate was similar to that of its parental strain S9026 in O3SF25 medium. Growth rates were estimated as similar if a 1-5% v/v inoculum into modified O3SF25 medium containing 0.25 mM Cl was able to achieve OD 3-6 within 24 hrs. The final subculture (designated S9026-MF5-1-0.25 mM Cl) was plated on GYPS agar and single colonies were screened for lipid production.

TABLE 9

Composition of defined or modified O3SF25 medium

| Components | Defined O3SF25 (8.4 mM Cl) | Modified O3SF25 (0.25-0.5 mM Cl) |
|---|---|---|
| $KH_2PO_4$ | 0.45 g/L | 0.45 g/L |
| $(NH_4)_2SO_4$ | 1.25 g/L | 1.25 g/L |
| $Na_2SO_4$ | 12 g/L | 12 g/L |
| $MgSO_4$•$7H_2O$ | 0.45 g/L | 0.45 g/L |
| KCl | 0.5 g/L | 0.02-0.04* g/L |
| $CaCl_2$•$2H_2O$ | 0.11 g/L | — |
| $CaSO_4$•$2H_2O$ | — | 0.13 g/L |
| Glucose | 60 g/L | 60 g/L |
| 1M Citrate buffer (pH 5.0 with KOH) | 50 mL/L | 50 mL/L |
| C-Trace 7 (Trace Metal Stock Solution) | 0.2 mL/L | 0.2 mL/L |
| DAS 3 (Sterile Vitamin Stock Solution) | 0.1 mL/L | 0.1 mL/L |
| Antifoam Sigma 204 | 0.225 mL/L | 0.225 mL/L |

1. Medium adjusted to pH 5.5 with NaOH.
2. Sterilize medium by filtration through a 0.22 μm PES filter.
*Target chloride level in medium with addition of appropriate qty of KCl

TABLE 10

Composition of DAS3 vitamin stock solution

| Components | Concentration |
|---|---|
| D-Pantothenic Acid Hemicalcium Salt | 3.7 g/L |
| Thiamine Hydrochloride | 3.7 g/L |
| Cyanocobalamine | 0.2 g/L |

1. Sterilize medium by filtration through a 0.22 μm PES filter.

TABLE 11

Composition of C-Trace 7 (trace metal stock solution)

| Components | Concentration |
|---|---|
| $MnCl_2$•$4H_2O$ | 8.18 g/L |
| $ZnSO_4$•$7H_2O$ | 8.18 g/L |
| $NaMoO_4$•$2H_2O$ | 0.11 g/L |
| $CuSO_4$•$5H_2O$ | 5.45 g/L |
| $NiSO_4$•$6H_2O$ | 5.45 g/L |
| $FeSO_4$•$7H_2O$ | 26.8 g/L |
| citric acid•H2O | 44 g/L |

1. Sterilized by heat in an autoclave at 121° C. for 35 min 80 isolates picked from S9026-MF5-1-0.25 mM Cl were screened in 50-mL bioreactor tubes containing 10 mL modified O3SF25 medium with 0.25 mM chloride as follows. Each isolate was inoculated into 0.8 mL modified O3SF25 medium (0.25 mM Cl) in 96-well block cultivation format, and then incubated at 28° C. and 900 rpm on multitron shaker for 20-24 h to prepare the primary seed cultures. The resulting primary seed cultures were inoculated at 4% (v/v) into 9.6 mL modified O3SF25 medium (0.5 mM chloride) in 50-mL bioreactor tubes. The production bioreactor tubes were incubated at 28° C. and 200 rpm on a rotary shaker for 3 days and then harvested for lipid assay. The parental strain S9026 was also cultivated in O3SF25 (8.4 mM Cl) in parallel as control.

Two isolates with good lipid productivity and DHA content in lipid were identified from primary screening and then cryopreserved as S9179 and S9180, respectively. After cryopreservation, S9179 and S9180 were confirmed to give good lipid production and DHA content in lipid comparable to the parent strain in reduced chloride medium (modified O3SF25 with 0.5 mM Cl).

S9179 and S9180 were also evaluated in 3-L laboratory-scale fermentors (Applikon, The Netherlands) in high cell-density fed-batch fermentation process using 350 mM NH4, N/P16 comparable to that used for evaluation of S9026. For cultivation of S9026, the seed stages typically comprised cultivation in O3SF25 (8.4 mM Cl) in flasks and inoculated at 10% v/v into production medium containing 10-11 mM Cl. For evaluation of S9179 and S9180, seed flask stages were cultivated in modified O3SF25 (0.25 mM Cl) and the production medium was modified to achieve 1 mM Cl (Table 12). To facilitate sucrose hydrolysis, 1.5 mL/L of 20 g/L Maxvert invertase solution (filter-sterilized) was added at the beginning of the fermentation runs.

The cultures were cultivated at 28° C. with an aeration rate of 1.0 vvm. Sterilized VHP syrup (70% w/w) was used as the carbon feedstock and was fed using a DO-responsive algorithm (on-demand pulsed-feeding to target <10 g/L total sugar per shot). The pH was maintained at 5.1±0.2 automatically by the addition of acid (16% w/w H2SO4) and base (28% w/w ammonium hydroxide followed by 10% w/w NaOH). Dissolved oxygen (DO) level was maintained at >20% of air saturation by automatic control of agitation (500-1250 rpm) followed by pure oxygen supplementation (0-100%). Ammonium sulfate (50 mM NH4+ batched) and ammonium hydroxide (300 mM NH4+) were used as the nitrogen source. As required, fermentation broth was sampled to determine the DCW, lipid titer and fatty acid composition, total solids and residual sugar concentrations in the broth.

TABLE 12

Composition of defined fermentation medium batched in fermentor

| Components | S9026 Fermentation Medium | Reduced Cl Fermentation Medium |
|---|---|---|
| $KH_2PO_4$ | 2.94 g/L | 2.94 g/L |
| $(NH_4)_2SO_4$ | 3.3 g/L | 3.3 g/L |
| $Na_2SO_4$ | 12 g/L | 12 g/L |
| $MgSO_4$•$7H_2O$ | 2.68 g/L | 2.68 g/L |
| KCl | 0.5 g/L | 0.06 g/L |
| $CaSO_4$•$2H_2O$ | — | 0.26 g/L |
| $CaCl_2$•2H2O | 0.22 g/L | — |
| Antifoam Sigma 204 | 0.225 mL/L | 0.225 mL/L |
| VHP70 sucrose | 40 g/L | 40 g/L |
| C-trace 7 | 1.83 mL/L | 1.83 mL/L |
| DAS3 | 4.21 mL/L | 4.21 mL/L |

Both strains S9179 and S9180 showed comparable strain performance on biomass and lipid production/yield, DHA content in lipid and DHA productivity/yield in the fermentors.

Although this invention has been described in connection with specific embodiments thereof, it will be understood that it is capable of further modifications. This application is intended to cover any variations, uses, or adaptations of the invention following, in general, the principles of the invention and including such departures from the present disclosure as come within known or customary practice within the art to which the invention pertains and as may be applied to the features hereinbefore set forth.

What is claimed:

1. A formulated feed comprising
edible food and
a feed ingredient composition, the feed ingredient composition comprising:
a dispersion of lysed microalgal cells in triglyceride oil, wherein:
a. 5-90% by weight of the feed ingredient composition is lysed microalgal cells, and
b. 10-95% by weight of the feed ingredient composition is triglyceride oil, wherein the triglyceride oil comprises oil from the lysed cells and oil from another organism,
the oil from the lysed cells has a fatty acid profile including 40-70% docosahexaenoic acid (DHA) by weight of the fatty acids in the oil from the lysed cells, and
wherein the feed ingredient composition is comprised of 12-45% by weight of DHA.

2. The formulated feed of claim 1, wherein the formulated feed is aquaculture feed.

3. The formulated feed of claim 2, wherein the formulated feed is salmon feed or shrimp feed.

4. The formulated feed of claim 1, wherein in total the triglyceride oil has a fatty acid profile of 10-70% DHA by weight of fatty acids in the triglyceride oil.

5. The formulated feed of claim 1, wherein the lysed cells have an aspect ratio of less than 1:1.

6. The formulated feed of claim 1, wherein the oil from the another organism is oil from a fish, plant, oleaginous microbe, animal, or combinations thereof.

7. The formulated feed of claim 1, wherein the microalgal cells are from the family Thraustochytriacae.

8. The formulated feed of claim 7, wherein the microalgal cells are from the genus selected from the group consisting of *Crypthecodinium, Thraustochytrium, Aurantiochytrium*, and *Schizochytrium.*

9. The formulated feed of claim 1, wherein said formulated feed is in pelletized form.

10. The formulated feed composition of claim 1, wherein the oil from another organism is a plant oil.

11. The formulated feed composition of claim 10, wherein the plant oil is coconut, corn, cottonseed, olive, palm, peanut, rapeseed, canola, safflower, sesame, soybean, nut, camelina, or citrus, or one or more combinations thereof.

12. The formulated feed of claim 1, wherein the oil from the another organism is an oil extracted and separated from the another organism.

13. The formulated feed of claim 1, wherein the microalgal cells are from the genus selected from the group consisting of *Thraustochytrium*, and *Schizochytrium.*

14. The formulated feed of claim 1, wherein the edible food is in a form of pressed or extruded feed, and the dispersion is coated onto the pressed or extruded food.

15. The formulated feed of claim 1, wherein 40-90% by weight of the feed ingredient composition is lysed microalgal cells, and 10-60% by weight of the feed ingredient composition is triglyceride oil, and wherein the oil from the lysed cells has a fatty acid profile including 50-70% DHA by weight of the fatty acids in the oil from the lysed cells.

16. A method for preparing the formulated feed of claim 1, the method comprising contacting the feed ingredient composition with the edible food.

* * * * *